(12) United States Patent
Husson et al.

(10) Patent No.: US 8,030,335 B2
(45) Date of Patent: Oct. 4, 2011

(54) USE OF LIVER X RECEPTOR AGONISTS

(75) Inventors: Bernadette Husson, Saint Apollinaire (FR); Pierre Broqua, Antony (FR); Jean-Louis Junien, Sevres (FR)

(73) Assignee: Laboratoires Fournier S.A., Dijon (FR)

( * ) Notice: Subject to any disclaimer, the term of this patent is extended or adjusted under 35 U.S.C. 154(b) by 772 days.

(21) Appl. No.: 11/920,141

(22) PCT Filed: May 10, 2006

(86) PCT No.: PCT/EP2006/062208
§ 371 (c)(1),
(2), (4) Date: Nov. 9, 2007

(87) PCT Pub. No.: WO2006/120213
PCT Pub. Date: Nov. 16, 2006

(65) Prior Publication Data
US 2009/0118306 A1 May 7, 2009

Related U.S. Application Data

(60) Provisional application No. 60/679,768, filed on May 10, 2005.

(51) Int. Cl.
*A61K 31/44* (2006.01)
*A61K 31/18* (2006.01)
(52) U.S. Cl. .......................... 514/352; 514/601; 514/866
(58) Field of Classification Search .................. 514/601, 514/352, 592, 635, 866
See application file for complete search history.

(56) References Cited

U.S. PATENT DOCUMENTS

| | | | |
|---|---|---|---|
| 6,316,503 B1 | 11/2001 | Li et al. | |
| 6,924,311 B2 * | 8/2005 | Schulman et al. | 514/601 |
| 2003/0073614 A1 | 4/2003 | Schulman et al. | |
| 2005/0036992 A1 | 2/2005 | Saez et al. | |

FOREIGN PATENT DOCUMENTS

| | | |
|---|---|---|
| EP | 1 398 032 | 3/2004 |
| WO | WO 90/11296 A1 | 10/1990 |
| WO | WO 98/43658 A1 | 10/1998 |
| WO | WO 99/43705 A1 | 9/1999 |
| WO | WO 01/41704 A2 | 6/2001 |
| WO | WO 2006/094034 A1 | 9/2006 |

OTHER PUBLICATIONS

Cao et al., "Antidiabetic Action of a Liver X Receptor Agonist Mediated By Inhibition of Hepatic Gluconeogenesis", The Journal of Biological Chemistry, vol. 278, No. 2, pp. 1131-1136 (2003).*
Beers et al., The Merck Manual of Medical Information, 2nd Home Edition, pp. 968 and 969 (2003).*
International Search Report, dated Mar. 30, 2007 (PCT/ISA/210) including PCT/ISA/220 and PCT/ISA/237 (Ten (10) pages).
Efanov, A. M. et al., "Liver X Receptor Activation Stimulates Insulin Secretion via Modulation of Glucose and Lipid Metabolism in Pancreatic β-Cells", Diabetes, Dec. 2004, pp. S75-S78, vol. 53, Supplement 3.
Steffensen, K. R. et al., "Section II: Nuclear Receptors and Islet Function—Putative Metabolic Effects of the Liver X Receptor (LXR)", Diabetes, Feb. 2004, pp. S36-S42, vol. 53, Supplement 1.
Cao, G. et al., "Antidiabetic Action of a Liver X Receptor Agonist Mediated by Inhibition of Heptic Gluconeogenesis", The Journal of Biological Chemistry, Jan. 10, 2003, pp. 1131-1136, vol. 278, No. 2.
Menke, J. G. et al., "A Novel Liver X Receptor Agonist Establishes Species Differences in the Regulation of Cholesterol 7 α-Hydroxylase (CYP7a)", Endocrinology, 2002, pp. 2548-2558, vol. 143, No. 7.
Janowski, B. A. et al., "An oxysterol signaling pathway mediated by the nuclear receptor LXRα", Nature, Oct. 24, 1996, pp. 728-731, vol. 383.
Schultz, J. R. et al., "Role of LXRs in control of lipogenesis", Genes and Development, 2000, pp. 2831-2838, vol. 14.
Joseph, S. B. et al., "Synthetic LXR ligand inhibits the development of atherosclerosis in mice", PNAS, May 28, 2002, pp. 7604-7609, vol. 99, No. 11.
Collins, J. L. et al., "Identification of a Nonsteroldal Liver X Receptor Agonist through Parallel Array Synthesis of Tertiary Amines", J. Med. Chem., 2002, pp. 1963-1966, vol. 45.
Janowski, B. A. et al., "Structural requirements of ligands for the oxysterol liver X receptors LXRα and LXRβ", Proc. Natl. Acad. Sci., Jan. 1999, pp. 266-271, vol. 96, Pharmacology.
Berger, J. et al., "Novel Peroxisome Proliferator-activated Receptor (PPAR) γ and PPARδ Ligands Produce Distinct Biological Effects", The Journal of Biological Chemistry, Mar. 5, 1999, pp. 6718-6725, vol. 274, No. 10.
Spencer, T. A. et al., "Pharmacophore Analysis of the Nuclear Oxysterol Receptor LXRα", J. Med. Chem, 2001, pp. 886-897, vol. 44.
Sparrow, C. P. et al., "A Potent Sythetic LXR Agonist Is More Effective than Cholesterol Loading at Inducing ABCA1 mRNA and Stimulating Cholesterol Efflux",. The Journal of Biological Chemistry, Mar. 22, 2002, pp. 10021-10027, vol. 277, No. 12.
Liao, K. et al., "The Blockade of Preadipocyte Differentiation by Protein-tyrosine Phosphatase HA2 Is Reversed by Vanadate", The Journal of Biological Chemistry, May 19, 1995, pp. 12123-12132, vol. 270, No. 20.
Efanov et al., "Liver X Receptor Activation Stimulates Insulin Secretion via Modulation of Glucose and Lipid Metabolism in Pancreatic Beta-Cells," Diabetes, vol. 53, Supplement 3. Dec. 2004, S75-S78.
Chisholm et al., "The LXR ligand T0901317 induces severe lipogenesis in the db/db diabetic mouse," Journal of Lipid Research, vol. 44, 2003, 2039-2048.

* cited by examiner

Primary Examiner — Kevin E Weddington
(74) Attorney, Agent, or Firm — Crowell & Moring LLP

(57) ABSTRACT

The present invention generally relates to a novel therapeutical use of liver X receptor (LXR) agonsits. More specifically, the present invention relates to the use of LXR agonist for the preparation of a medicament useful for the treatment and/or the prevention of a disease associated with beta cells degeneration, such as diabetes, and a method for increasing ex vivo viability of pancreatic islet cells, comprising contacting said islet cells with a LXR agonist.

8 Claims, 7 Drawing Sheets

Values represent mean ± s.e.mean n= 6 to 7 rats.

Values represent mean ± s.e.mean n= 6 to 7 rats

Values represent mean ± s.e.mean n= 6 to 9 rats

Values represent mean ± s.e.mean n= 4 to 7 rats

USE OF LIVER X RECEPTOR AGONISTS

FIELD OF THE INVENTION

The present invention generally relates to a novel therapeutical use of liver X receptor (LXR) agonsits. More specifically, the present invention relates to the use of LXR agonist for the preparation of a medicament useful for the treatment and/or the prevention of a disease associated with beta cells degeneration, such as diabetes, and a method for increasing ex vivo viability of pancreatic islet cells, comprising contacting said islet cells with a LXR agonist.

BACKGROUND OF THE INVENTION

Diabetes is generally classified in two main groups. In type I diabetes, auto-immune destruction of beta cells within the islets of Langerhans leads to a marked defect in insulin production. In contrast, type II diabetes is characterized by insulin resistance in muscle, fat, and liver along with a relative impairment of insulin production in beta cells. Multiple genes contribute to susceptibility in both type I and type II diabetes, although in most cases their identities remain unknown.

Apoptosis is an active process of cellular self-destruction that is regulated by extrinsic and intrinsic signals occurring during normal development. It is well documented that apoptosis plays a key role in the plasticity of pancreatic endocrine beta cells. There is increasing evidence that in adult mammalians the beta-cell mass is submitted to dynamic changes to adapt insulin production for maintaining euglycemia in particular conditions, such as pregnancy and obesity. The control of beta cell mass depends on a subtle balance between cell proliferation, growth and cell death (apoptosis). A disruption of this balance may lead to impairment of glucose homeostasis. For example, it is noteworthy that glucose intolerance develops with aging when the replication rate of beta cell is reduced and that patients with non-insulin-dependent-diabetes mellitus have a 40-60% loss of beta cell mass as compared with nondiabetic subjects. It is generally agreed that, in insulino-resistant subjects, normoglycemia is maintained by compensatory hyperinsulinemia until the beta cells become unable to meet the increased demand for insulin, at which point Type II Diabetes breaks out.

Type II or noninsulin-dependent diabetes mellitus (NIDDM) is a polygenic disease and accounts for >90% of diabetes cases. This disease is characterized by resistance to insulin action on glucose uptake and impaired insulin action to inhibit hepatic glucose production.

Regulation of glucose metabolism by insulin is a key mechanism by which homeostasis is maintained in an animal. Insulin stimulates uptake of glucose from the blood into tissues, especially muscle and fat. This occurs via increased translocation of Glut4, the insulin-sensitive glucose transporter, from an intracellular vesicular compartment to the plasma membrane. Glut4 is the most important insulin-sensitive glucose transporter in these tissues. Insulin binds to its receptor in the plasma membrane, generating a series of signals that result in the translocation or movement of Glut4 transporter vesicles to the plasma membrane.

Liver X receptors (LXRs) are members of a nuclear receptor superfamily that induce ligand dependent transcriptional activation of target genes. They play important roles in cholesterol metabolism and homeostasis. Two LXR proteins (alpha and beta) are known to exist in mammals. LXRalpha expression is high in organs involved in lipid homeostasis such as intestin, brown and white adipose tissues whereas LXRbeta is more ubiquitous and enriched in tissues of neuronal and endocrine origin. Recently, LXRalpha and beta have been found expressed in pancreatic islets as well as alpha cells and beta cells (Efanov et al, Diabetes, 53(3), S75-78, 2004).

LXRalpha and LXRbeta are closely related and share 77% amino acid identity in both their DNA- and ligand-binding domains. The LXRs are also conserved between humans and other animals (e.g., rodents). Like other nuclear receptors, LXRs heterodimerize with retinoid X receptor (RXR) for function. LXRs are known to be activated by certain naturally occurring, oxidized derivatives of cholesterol, including 22(R)-hydroxycholesterol, 24(S)-hydroxycholesterol and 24,25(S)-epoxycholesterol.

LXRalpha and beta are regulators of hepatic genes involved in cholesterol and fatty acid metabolism (HMGCOA synthase/reductase, farnesyl diphosphate synthase, squalene synthase, SREBP1c, stearoyl CoA desaturase (SCD1 and 2), FAS), inhibits expression of gluconeogenic enzymes (PEPCK, fructose biphosphatase1, glucose 6 phosphatase), induce expression of transmembrane transporter (ABCA1, Glut1 and Glut4), inhibit expression of enzymes involved in glycolysis (6-phosphofructo-2-kinase) and induce pyruvate dehydrogenase kinase 4 (a negative regulator of glycolysis), decrease 11-betahydroxysteroid dehydrogenase type 1 (enzyme that reactivates inactive cortisone in active cortisol in humans). Leptin and UCP-1 have been identified as target genes of LXR (down regulation by LXR agonists). Moreover, LXRs have overlapping functions with PPARs in the negative control of the inflammatory response. LXRs inhibit the production of TNFα and IL-1β and the expression of inflammatory mediators such as COX2, iNOS, IL-6. LXR may play a key role in responses to inflammation, and because it has been shown to be important in lipid metabolism, LXR might be involved in obesity-induced inflammatory responses as well. (reviewed in Steffensen et al, Diabetes, 2004, 53(1), S36-42).

In db/db mice, T0901317, a LXR agonist described herebelow, has shown to lower plasma glucose level (not in normal mice). This compound inhibits the expression of PEPCK to limit hepatic glucose output (Cao et al, J Biol Chem, 2003, 278, 1131-1136).

Culture of pancreatic islets or insulin-secreting MIN6 cells with T0901317 caused an increase in glucose-dependent insulin secretion and islet insulin content. The stimulatory effect of this compound on insulin secretion was observed only after >72 h of islet culture with T0901317. In MIN6 cells, Tularik increased protein expression of lipogenic enzymes, fatty acid synthase and acetyl-CoA carboxylase. LXR activation also produced an increase in glucokinase protein and pyruvate carboxylase (PC) activity levels. LXRs could control insulin secretion and biosynthesis via regulation of glucose and lipid metabolism in pancreatic beta cell (Efanov et al, Diabetes, 53(3), S75-78, 2004).

The pancreatic duodenal homeobox gene-1 (Pdx-1) is a master regulator of both pancreatic development and the differentiation of progenitor cells into the beta cell phenotype. Moreover, in the differentiated beta cell, Pdx1 is a glucose-responsive regulator of insulin gene expression and the function of Pdx1 in response to glucose is regulated by both its phosphorylation and nuclear translocation. During the later stages of islet development, the expression of Pdx-1 becomes mostly restricted to the mature beta cells of the endocrine pancreas. In the adult pancreas, subpopulations of somatostatin-producing and pancreatic polypeptide-producing cells also express Pdx-1, only a few glucagon-producing cells express it.

A defect in glucose sensing of the pancreatic beta cells has been observed in several animal models of type II diabetes and has been correlated with a reduced gene expression of the glucose transporter type 2 (Glut2). In a transgenic mouse model, expression of Glut2 antisense RNA in pancreatic beta-cells has been shown to be associated with an impaired glucose-induced insulin secretion and the development of diabetes. The glucose transporter type 2 (GLUT2) gene expression is selectively decreased in the beta-pancreatic cells of experimental models of diabetes and the murine GLUT2 promoter is controlled by PDX-1.

SUMMARY OF THE INVENTION

The present invention is based in part on the unexpected discovery that activation of LXRs in ZDF rats leads to the improvement of diabetic state with a significant decrease of glycemia after treatment with a LXR agonist. In assessing potential mechanisms underlying the antidiabetic action of the LXR agonist, a significant reduction of apoptosis in isolated islets from ZDF rats treated with the known LXR agonist named "GW3965" associated with an increase of the islets number has unexpectedly been found; in addition, these islets had a significantly larger content of insulin and a better glucose sensitivity than those from vehicle-treated ZDF rats. These discoveries and additional experimental work have shown that in vivo LXR agonist administration is able to stimulate insulin secretion while protecting the pancreatic islets from deterioration.

Moreover, it has been shown that a significant increase in mRNA level of PDX1 and Glut2, two major genes involved in islet regeneration, was obtained in islets of ZDF rats treated with GW3965. The regeneration of pancreatic islets has also been confirmed by pancreatic histological analysis of GW3965 treated-NOD mice.

The present invention is also based on the new discovery that a LXR agonist not only protects the diabetic pancreas from further deterioration, in particular by reducing apoptosis and insulitis in pancreas, but also enhances pancreatic regenerative processes and, thus, allows to restore the pancreatic function when it becomes compromise. These effects are additional to the decrease of hepatic glucose output described in liver (Cao et al, 2003, JBC, 278(2), 1131-1136) and potentiate the antidiabetic properties of LXRs agonists.

The beneficial property of LXR agonists to increase the number of islets and to reduce the apoptosis in islets permits a new mode of treatment: it consists in treating patients for a limited period of time until glycemia and/or HbA1c (A1c haemoglobin) are reduced to a steady-state level (HbA1C≦7% and/or glycemia≦1.2-1.4 g/l); then, treatment is suspended as long as glycemia and/or HbA1c remain in an acceptable range (for example for one month). If glycemia and/or HbA1c level increase above acceptable values, a treatment with the LXR agonist would then be prescribed again.

In a first aspect, the present invention is therefore directed to the use of a LXR agonist for the preparation of a medicament useful for the treatment and/or the prevention of a disease associated with beta cells degeneration.

The present invention is also directed to the use of a LXR agonist for the preparation of a medicament useful for the regeneration of beta cells and for increasing the viability of beta cells.

The use according to the invention provides a medicament that can be used in association with a known anti-diabetic drug.

In a second aspect, the present invention is directed to a method for increasing ex vivo viability of primary pancreatic islet cells, comprising contacting said islet cells with a LXR agonist.

In a third aspect, the present invention provides methods for treatment of beta cell degeneration, comprising administering a LXR agonist to a subject.

In a first embodiment, the invention provides methods for preventing type I diabetes in a subject, comprising administering an effective amount of a LXR agonist to a subject.

In another embodiment, the present invention provides methods for treating or ameliorating diabetes, the method comprising measuring circulating glucose level and/or HbA1c in the subject and administering daily to the subject an effective amount of a LXR agonist until stabilisation of the glycemia and/or HbA1c (HbA1C≦7% and/or glycemia≦1.2-1.4 g/l maintained for one month with at least two dosages), then stopping the treatment once the glycemia and/or HbA1c is stabilised; the daily treatment being optionally reconducted if necessary.

In another embodiment, the invention provides methods for increasing the viability of transplanted donor pancreatic islet cells in a transplant recipient, comprising administering to said transplant recipient a LXR agonist.

A further understanding of the nature and advantages of the present invention may be realized by reference to the remaining portions of the specification and claims.

DETAILED DESCRIPTION

In one aspect, the present invention is directed to the use of a LXR agonist for the preparation of a medicament useful for the treatment and/or the prevention of a disease associated with beta cells degeneration.

The use according to the present invention finds application in treating diseases associated in particular with a loss of beta cell function or beta cell dysfunction and/or death of beta cells, such as, but not limited to, diabetes, hyperglycemia and obesity. The present invention is also useful for preventing or modulating the development of such diseases or disorders in a subject suspected of being, or known to be, prone to such diseases or disorders.

The present invention is thus related to the use of a L)(R agonist for the preparation of a medicament useful for the treatment and/or the prevention of type I and type II diabetes, and preferably of type I diabetes.

As explained above, type II diabetic patients can exhibit more or less type I diabetes features, mainly related with insulin production deficiency. Accordingly, in one embodiment, the present invention is directed to the use of a LXR agonist for the preparation of a medicament useful for preventing, halting or slowing the progression of type II diabetes towards subsequent diabetic state characterized by insulin production deficiency.

As in vivo LXR agonist administration increases the number of islets and to reduce the apoptosis in islets, the use of a LXR agonist for the preparation of a medicament useful for the regeneration of beta cells and for increasing the viability of beta cells represents two additional embodiments of the present invention.

With regard to the use for increasing the viability of pancreatic cells, it should be understood that viable cells are defined as capable of proliferation, differentiation, growth and development. Viability can be measured by any methods known in the art, and for example by using trypan blue staining.

In another embodiment, the present invention is directed to the use of a LXR agonist for the preparation of a medicament useful for increasing the viability of transplanted donor pancreatic islet cells in a transplant recipient. The pancreatic islet cells are primary islet cells.

For this particular application, the medicament can be administered locally to a transplanted site or preferably administered systemically.

In one embodiment, the medicament is administered to the transplant recipient prior to and/or after transplantation of donor pancreatic islet cells. In another embodiment, the medicament is administered to the transplant recipient concurrently with the transplantation of donor pancreatic.

Any LXR agonists known and described in the art can be used in order to practice all the uses and methods as described herein according to the present invention. Preferably, the LXR agonist is a LXRalpha agonist, and in particular the LXR agonist is selected from the group consisting of GW3965 and T0901317.

In addition, according to an advantageous embodiment, the medicament to be used for all the uses and methods of the present invention, is in a form suitable for oral administration.

In all uses and methods described herein, the medicament is preferably administered daily for at least 30 days. It can also be administered for at least 60 days, 90 days, or longer.

In addition, the medicament according to the present invention can be used in association with a known anti-diabetic drug, and in particular one selected from the group consisting of metformin, pioglitizone, rosiglitazone, glimepiride, glipizide, glyburide/metformin, glyburide, miglitol, glipizide+metformin, repaglinide, acarbose, troglitazone, nateglinide, and a GLP-1 (Glucagon-Like Peptide-1) agonist.

In a second aspect, the present invention is directed to a method for increasing ex vivo viability of primary pancreatic islet cells, comprising contacting said islet cells with a LXR agonist.

Preferably, the LXR agonist is an LXRalpha agonist, and in particular the LXR agonist to be used is selected from the group consisting of GW3965 and T0901317.

In a third aspect, the present invention provides methods for treatment of beta cell degeneration. The methods entail administering to a subject a LXR agonist. In such methods, the LXR agonist employed can be a LXRalpha agonist, and in particular the LXR agonist to be used is selected from the group consisting of GW3965 and T0901317.

In the methods according to the invention, the subject is preferably suffering from type I or type II diabetes. Optionally, the LXR agonist is administered simultaneously with a known anti-diabetic drug to the subject, or with any other drug reducing glycemia and/or HbA1c. In particular, the known anti-diabetic drug is selected from the group consisting of metformin, pioglitizone, rosiglitazone, glimepiride, glipizide, glyburide/metformin, glyburide, miglitol, glipizide+metformin, repaglinide, acarbose, troglitazone, nateglinide, and a GLP-1 agonist.

In one embodiment, the invention provides methods for preventing type I diabetes in a subject. The methods comprise administering to a subject an effective amount of a LXR agonist. Similarly, the LXR agonist employed in said methods for preventing type I diabetes can be a LXRalpha agonist, and in particular the LXR agonist to be used is selected from the group consisting of GW3965 and T0901317.

Optionally, the LXR agonist is administered simultaneously with a known anti-diabetic drug to the subject, or with any other drug reducing glycemia and/or HbA1c. In particular, the known anti-diabetic drug is selected from the group consisting of metformin, pioglitizone, rosiglitazone, glimepiride, glipizide, glyburide/metformin, glyburide, miglitol, glipizide+metformin, repaglinide, acarbose, troglitazone, nateglinide, and a GLP-1 agonist.

In another aspect, the present invention provides methods for treating or ameliorating diabetes, the method comprising measuring circulating glucose level and/or HbA1c in the subject and administering daily to the subject an effective amount of a LXR agonist until stabilisation of the glycemia and/or HbA1c (HbA1C≦7% and/or glycemia≦1.2-1.4 g/l maintained for one month with at least two dosages), then stopping the treatment once the glycemia and/or HbA1c is stabilized; the daily treatment being optionally reconducted if necessary.

The daily treatment can optionally be reconducted if the glycemia and/or HbA1c is no more stabilised or insulin sensitivity is lost.

Methods for measuring circulating glucose and/or HbA1c levels are the methods well known in the prior art and any kind of methods can be used.

Similarly, the LXR agonist employed in said methods for treating or ameliorating diabetes can be a LXRalpha agonist, and in particular the LXR agonist to be used is selected from the group consisting of GW3965 and T0901317. Optionally, the LXR agonist is administered simultaneously with a known anti-diabetic drug to the subject, or with any other drug reducing glycemia and/or HbA1c. In particular, the known anti-diabetic drug is selected from the group consisting of metformin, pioglitizone, rosiglitazone, glimepiride, glipizide, glyburide/metformin, glyburide, miglitol, glipizide+metformin, repaglinide, acarbose, troglitazone, nateglinide, and a GLP-1 agonist.

In said methods, the LXR agonist is preferably administered to the subject at least daily for at least 30 days.

In another embodiment, the present invention is directed to a method for increasing the viability of transplanted donor pancreatic islet cells in a transplant recipient, comprising administering to said transplant recipient a LXR agonist.

The following sections provide guidance for making and using the medicament according to the invention, and for carrying out the methods of the invention.

DEFINITIONS

Unless defined otherwise, all technical and scientific terms used herein have the same meaning as commonly understood by those of ordinary skill in the art to which this invention pertains. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). In addition, the following definitions are provided to assist the reader in the practice of the invention.

The term "LXR" (liver X receptor) or "LXR receptor" includes all subtypes of this receptor. Specifically LXR includes LXRalpha and LXRbeta. LXRalpha has been referred to under a variety of names such as LXRU, LXRa, LXR, RLD-1, NR1H3. It encompasses any polypeptide encoded by a gene with substantial sequence identity to GenBank accession number U22662. Similarly, LXRbeta included any polypeptide encoded by a gene referred to as LXRb, LXRP, LXRbeta, NER, NER1, UR, OR-1, RIP 15, NR1H2 or a gene with substantial sequence identity to GenBank accession number U07132.

The term "ligand" refers to an agonist or partial agonist of LXR. The ligand may be selective for LXRalpha or LXRbeta, or it may have mixed binding affinity for both LXRalpha and LXRbeta. While a ligand can either agonize or antagonize a receptor function, unless otherwise specified, a LXR ligand used herein primarily refers to a LXR agonist that activates the LXR receptor.

The term "modulate" with respect to a LXR receptor refers to activation of the LXR receptor and its biological activities associated with the LXR pathway (e.g., transcription regulation of a target gene). Modulation of LXR receptor can be up-regulation (i.e., agonism, activation or stimulation) or down-regulation (i.e. antagonism, inhibition or suppression). The mode of action of a LXR modulator can be direct, e.g., through binding to the LXR receptor as a ligand. The modulation can also be indirect, e.g., through binding to and/or modifying another molecule which otherwise binds to and activates the LXR receptor. Thus, modulation of LXR includes a change in the bioactivities of a LXR agonist ligand (i.e., its activity in binding to and/or activating a LXR receptor) or a change in the cellular level of the ligand.

As used herein, the phrase "screening for LXR agonists" refers to use of an appropriate assay system to identify novel LXR agonists from test agents. The assay can be an in vitro or an in vivo assay suitable for identifying whether a test agent can stimulate or activate one or more of the biological functions of the LXR receptor. Examples of suitable bioassays include, but are not limited to, assays for examining binding of test agents to an LXR polypeptide (e.g., LXR fragment containing its ligand binding domain), transcription-based assays, creatine kinase assays, assays based on the differentiation of pre-adipocytes, assays based on glucose uptake control in adipocytes, and immunological assays.

The "subject" is preferably a mammal, more preferably a human.

The term "beta cell degeneration" is intended to mean loss of beta cell function, beta cell dysfunction, and death of beta cells, such as necrosis or apoptosis of beta cells.

The term "treatment of a disease" is defined as the management and care of a patient for the purpose of combating the disease, condition, or disorder and includes the administration of a LXR agonist to prevent the onset of the symptoms or complications, or alleviating the symptoms or complications, or eliminating the disease, condition, or disorder. Treatment includes modulate, inhibit, decrease, reduce or arrest beta cell degeneration, such as necrosis or apoptosis of beta cells, in particular the programmed beta cell death known as apoptosis of beta cells as well as prevention of beta cell degeneration, such as necrosis or apoptosis of beta cells, in particular prevention of apoptosis of beta cells. Treatment includes also the regeneration of beta cells.

The term "for the treatment" as used herein is to be understood as covering the direct use of the compound for the treatment or the indirect use of said compound in a treatment for the specified disease.

The term "insulin production deficiency" is intended to mean exhibiting a significant hyperglycemia and normo- or hypo-insulinemia. Methods for measuring glycemia or insulin levels and estimating hyperglycemia and normo- or hypo-insulinemia are well known in the art.

The term "in association with" is intended to refer either to a medicament in which the two active principles (the LXR agonist and the anti-diabetic drug) are the essential constituents of the same composition, or to two separate medicaments that can be administered simultaneously or subsequently.

The terms "stabilisation of glycemia and/or HbA1c" or "once glycemia and/or HbA1c is stabilized" as used herein are intended to mean a HbA1C value$\leq$7% and/or a glycemia value$\leq$1.2-1.4 g/l maintained for one month with at least two dosages.

LXR Agonists

There are many LXR agonists that are suitable for practicing methods of the present invention. They can be known agents that activate LXR receptor, e.g., GW3965 (see Examples below), or other commercially available compounds such as F3-MethylAA (from Merck; see Menke et al., Endocrinology 143: 2548-58, 2002) and T0901317 (Tularik, Calif.). They can also be novel LXR agonists to be screened for in accordance with the present invention. As detailed below, the LXR agonists suitable for the present invention can be polypeptides, peptides, small molecules, or other agents. The LXR agonists can be agonists for LXR of human as well as other animals.

A great number of LXR agonists have been described in the art. Examples of small molecule LXR agonists include the well known oxysterols and related compounds (Janowski et al., Nature 383: 728-31, 1996); T0901317 and T0314407 (Schultz et al., Genes Dev 14: 2831-8, 2000); 24(S)-hydroxy-cholesterol, and 22(R)-hydroxycholesterol (Janowski et al., Nature 383: 728-731, 1996); and 24,25-epoxycholesterol (U.S. Pat. No. 6,316,503). Exemplary polypeptide agonists of LXR have also been disclosed in the art, e.g., WO 02/077229. Additional LXR agonists have been described in the art, e.g., in U.S. Pat. No. 6,316,503; Collins et al., J Med. Chem. 45: 1963-6, 2002; Joseph et al., Proc Natl Acad Sci USA 99: 7604-9, 2002; Menke et al., Endocrinology 143: 2548-58, 2002; Schultz et al., Genes Dev. 14: 2831-8, 2000; and Schmidt et al., Mol Cell Endocrinol. 155: 51-60, 1999.

Many LXR agonists are effective in activating both LXRalpha and LXRbeta (e.g., GW3965 as described in Collins et al., J Med. Chem. 45: 1963-6, 2002). Some LXR agonists activate LXRalpha and LXRbeta under different conditions. For example, 6-alpha-hydroxylated bile acids are agonists of LXRalpha, but also activate LXRbeta at higher concentrations (Song et al., Steroids 65: 423-7, 2000). Some LXR agonists act exclusively on LXRalpha, while some others activate only LXRbeta. For example, introduction of an oxygen on the sterol B-ring of oxysterol results in a ligand with LXRalpha-subtype selectivity (Janowski et al., Proc Natl Acad Sci USA 96: 266-71, 1999). Using ligand-dependent transcription assays, it was found that 5-tetradecyloxy-2-furancarboxylic acid (TOFA) and hydroxycholesterol trans-activates chimeric receptors composed of the glucocorticoid receptor DNA binding domain and the ligand binding regions of LXRbeta, PPARalpha, and PPARbeta receptors (Schmidt et al., Mol Cell Endocrinol. 155: 51-60, 1999).

LXR agonists can also be obtained from derivatives of known polypeptide agonists of the LXR receptor. They can be produced by a variety of art known techniques. For example, specific oligopeptides (e.g., 10-25 amino acid residues) spanning a known polypeptide agonist of LXR can be synthesized (e.g., chemically or recombinantly) and tested for their ability to activate an LXR receptor. The LXR agonist fragments can be synthesized using standard techniques such as those described in Bodansky, M. Principles of Peptide Synthesis, Springer Verlag, Berlin (1993) and Grant, G. A (ed.). Synthetic Peptides: A User's Guide, W. H. Freeman and Company, New York (1992). Automated peptide synthesizers are commercially available, e.g., from Advanced ChemTech Model 396; Milligen/Biosearch 9600. Alternatively, such LXR agonists can be produced by digestion of native or recombinantly produced polypeptide agonists of LXR using a protease, e.g., trypsin, thermolysin, chymotrypsin, or pepsin. Computer analysis (using commercially available software, e.g. MacVector, Omega, PCGene, Molecular Simulation, Inc.) can be used to identify proteolytic cleavage sites.

The polypeptide or peptide agonists for use in methods of the present invention are preferably isolated and substantially free of cellular material or other contaminating proteins from the cell or tissue source from which the LXR agonists is derived, or substantially free from chemical precursors or other chemicals when chemically synthesized. The proteolytic or synthetic polypeptide agonists or their fragments can comprise as many amino acid residues as are necessary to activate LXR receptor activity, and can comprise at least 5, 10, 15, 20, 25, 30, 35, 40, 45, 50, or more amino acids in length.

Other than known compounds and polypeptides that activate the LXR receptor, LXR agonists can also be obtained by screening test agents (e.g., compound libraries) to identify novel LXR agonists that bind to and/or activate LXR receptor activities. To screen for such novel LXR agonists, a human LXR or LXR of other animals can be employed in a proper assay system. Polynucleotide and amino acid sequences of the LXR receptors are known and described in the art. Their structures and functional organizations, including their ligand binding domains, have also been characterized. See, e.g., Apfel et al., Mol Cell Biol 14: 7025-7035, 1994; Willy et al., Genes Dev 9: 1033-1045, 1995; Song et al., Proc Natl Acad Sci USA 91: 10809-10813, 1994; Shinar et al., Gene 147: 273-276, 1994; Teboui et al., Proc Natl Acad Sci USA 92: 2096-2100, 1995; and Seol et al., Mol Endocrinol 9: 72-85, 1995.

The agonists can activate either LXR or LXRalpha. In addition, instead of the full length LXR molecule, some of the screen assays can employ an LXR polypeptide that comprises a fragment of an LXR molecule. For example, the two functional domains of the LXR receptor, the N-terminal DNA binding domain (DBD) and the C-terminal ligand-binding domain (LBD), mediate the transcriptional activation function of nuclear receptors. An LXR polypeptide containing any of these domains can be used in screening for novel LXR agonists.

A number of assay systems can be employed to screen test agents for agonists of an LXR receptor. As detailed below, test agents can be screened for direct binding to an LXR polypeptide or a fragment thereof (e.g., its ligand binding domain). Alternatively or additionally, potential LXR agonists can be examined for ability to activate LXR receptor pathway or stimulate other biological activities of the LXR receptor. Either an in vitro assay system or a cell-based assay system can be used in the screening.

Selectivity of potential LXR agonists for different receptors (e.g., LXRalpha, LXRbeta, RXR, or PPAR) can be tested using methods well known in the art, e.g., the LXR radioligand competition scintillation proximity assays described in, e.g., WO 01/41704, and the PPAR competition binding assays described in, e.g., Berger et al., J Biol Chem 274: 6718-6725, 1999).

Test agents that can be screened for novel LXR agonists include polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, polypeptides, saccharides, fatty acids, steroids, purines, pyrimidines, derivatives, structural analogs or combinations thereof. Some test agents are synthetic molecules, and others natural molecules.

Test agents are obtained from a wide variety of sources including libraries of synthetic or natural compounds. Combinatorial libraries can be produced for many types of compound that can be synthesized in a step-by-step fashion. Large combinatorial libraries of compounds can be constructed by the encoded synthetic libraries (ESL) method described in WO 95/12608, WO 93/06121, WO 94/08051, WO 95/35503 and WO 95/30642. Peptide libraries can also be generated by phage display methods (see, e.g., Devlin, WO 91/18980). Libraries of natural compounds in the form of bacterial, fungal, plant and animal extracts can be obtained from commercial sources or collected in the field. Known pharmacological agents can be subject to directed or random chemical modifications, such as acylation, alkylation, esterification, amidification to produce structural analogs.

Combinatorial libraries of peptides or other compounds can be fully randomized, with no sequence preferences or constants at any position. Alternatively, the library can be biased, i.e., some positions within the sequence are either held constant, or are selected from a limited number of possibilities. For example, in some cases, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, or to purines.

The test agents can be naturally occurring proteins or their fragments. Such test agents can be obtained from a natural source, e.g., a cell or tissue lysate. Libraries of polypeptide agents can also be prepared, e.g., from a cDNA library commercially available or generated with routine methods. The test agents can also be peptides, e.g., peptides of from about 5 to about 30 amino acids, with from about 5 to about 20 amino acids being preferred, and from about 7 to about 15 being particularly preferred. The peptides can be digests of naturally occurring proteins, random peptides, or "biased" random peptides. In some methods, the test agents are polypeptides or proteins.

The test agents can also be nucleic acids. Nucleic acid test agents can be naturally occurring nucleic acids, random nucleic acids, or "biased" random nucleic acids. For example, digests of prokaryotic or eukaryotic genomes can be similarly used as described above for proteins.

In some preferred methods, the test agents are small organic molecules (e.g., molecules with a molecular weight of not more than about 1,000). Preferably, high throughput assays are adapted and used to screen for such small molecules. In some methods, combinatorial libraries of small molecule test agents as described above can be readily employed to screen for small molecule modulators of an LXR receptor. A number of assays are available for such screening, e.g., as described in Schultz (1998) Bioorg Med Chem Lett 8: 2409-2414; Weller (1997) Mol. Divers. 3: 61-70; Fernandes (1998) Curr Opin Chem Biol 2: 597-603; and Sittampalam (1997) Curr Opin Chem Biol 1: 384-91.

Potential LXR agonists can also be identified based on rational design. For example, Janowski et al. (Proc Natl Acad Sci USA 96: 266-71, 1999) disclosed structural requirements of ligands for LXRalpha and LXRbeta. It was shown that position-specific monooxidation of the sterol side chain of oxysterol is requisite for LXR high-affinity binding and activation. Enhanced binding and activation can also be achieved through the use of 24-oxo ligands that act as hydrogen bond acceptors in the side chain. In addition, introduction of an oxygen on the sterol B-ring results in a ligand with LXRalpha-subtype selectivity.

Libraries of test agents to be screened with the claimed methods can also be generated based on structural studies of the LXR receptors, their fragments or analogs. Such structural studies allow the identification of test agents that are more likely to bind to the LXR receptor. The three-dimensional structure of an LXR receptor can be studied in a number of ways, e.g., crystal structure and molecular modeling. Methods of studying protein structures using x-ray crystallography are well known in the literature. See Physical Biochemistry, Van Holde, K. E. (Prentice-Hall, N.J. 1971), pp.

221-239, and Physical Chemistry with Applications to the Life Sciences, D. Eisenberg & D. C. Crothers (Benjamin Cummings, Menlo Park 1979). Methods of molecular modeling have been described in the literature, e.g., U.S. Pat. No. 5,612,894 entitled "System and method for molecular modeling utilizing a sensitivity factor", and U.S. Pat. No. 5,583,973 entitled "Molecular modeling method and system". In addition, protein structures can also be determined by neutron diffraction and nuclear magnetic resonance (NMR). See, e.g., Physical Chemistry, 4th Ed. Moore, W. J. (Prentice-Hall, N.J. 1972), and NMR of Proteins and Nucleic Acids, K. Wuthrich (Wiley-Interscience, New York 1986).

In some screening assays, binding of a test agent to an LXR or an LXR polypeptide containing its ligand binding domain is determined. Binding of test agents (e.g., polypeptides) to the LXR polypeptide can be assayed by a number of methods including, e.g., labeled in vitro protein-protein binding assays, electrophoretic mobility shift assays, immunoassays for protein binding, functional assays (phosphorylation assays, etc.), and the like. See, e.g., U.S. Pat. Nos. 4,366,241; 4,376,110; 4,517,288; and 4,837,168; and also Bevan et al., Trends in Biotechnology 13: 115-122, 1995; Ecker et al., Bio/Technology 13: 351-360, 1995; and Hodgson, Bio/Technology 10: 973-980, 1992. The test agent can be identified by detecting a direct binding to the LXR polypeptide, e.g., co-immunoprecipitation with the LXR polypeptide by an antibody directed to the LXR polypeptide. The test agent can also be identified by detecting a signal that indicates that the agent binds to the LXR polypeptide, e.g., fluorescence quenching.

Competition assays provide a suitable format for identifying test agents (e.g., peptides or small molecule compounds) that specifically bind to an LXR polypeptide. In such formats, test agents are screened in competition with a compound already known to bind to the LXR polypeptide. The known binding compound can be a synthetic compound. It can also be an antibody, which specifically recognizes the LXR polypeptide, e.g., a monoclonal antibody directed against the LXR polypeptide. If the test agent inhibits binding of the compound known to bind the LXR polypeptide, then the test agent also binds the LXR polypeptide.

Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9: 242-253 (1983)); solid phase direct biotin-avidin EIA (see Kirkland et al., J. Immunol. 137: 3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using $^{125}I$ label (see Morel et al., Mol. Immunol. 25(1):7-15 (1988)); solid phase direct biotin-avidin EIA (Cheung et al., Virology 176: 546-552 (1990)); and direct labeled RIA (Moldenhauer et al., Scand. J. Immunol. 32: 77-82 (1990)). Typically, such an assay involves the use of purified polypeptide bound to a solid surface or cells bearing either of these, an unlabelled test agent and a labeled reference compound. Competitive inhibition is measured by determining the amount of label bound to the solid surface or cells in the presence of the test agent. Usually the test agent is present in excess. Modulating agents identified by competition assay include agents binding to the same epitope as the reference compound and agents binding to an adjacent epitope sufficiently proximal to the epitope bound by the reference compound for steric hindrance to occur. Usually, when a competing agent is present in excess, it will inhibit specific binding of a reference compound to a common target polypeptide by at least 50 or 75%.

The screening assays can be either in insoluble or soluble formats. One example of the insoluble assays is to immobilize an LXR polypeptide or its fragments onto a solid phase matrix. The solid phase matrix is then put in contact with test agents, for an interval sufficient to allow the test agents to bind. After washing away any unbound material from the solid phase matrix, the presence of the agent bound to the solid phase allows identification of the agent. The methods can further include the step of eluting the bound agent from the solid phase matrix, thereby isolating the agent. Alternatively, other than immobilizing the LXR polypeptide, the test agents are bound to the solid matrix and the LXR polypeptide molecule is then added.

Soluble assays include some of the combinatory libraries screening methods described above. Under the soluble assay formats, neither the test agents nor the LXR polypeptide are bound to a solid support. Binding of an LXR polypeptide or fragment thereof to a test agent can be determined by, e.g., changes in fluorescence of either the LXR polypeptide or the test agents, or both. Fluorescence may be intrinsic or conferred by labeling either component with a fluorophor.

In some binding assays, either the LXR polypeptide, the test agent, or a third molecule (e.g., an antibody against the LXR polypeptide) can be provided as labeled entities, i.e., covalently attached or linked to a detectable label or group, or cross-linkable group, to facilitate identification, detection and quantification of the polypeptide in a given situation. These detectable groups can comprise a detectable polypeptide group, e.g., an assayable enzyme or antibody epitope. Alternatively, the detectable group can be selected from a variety of other detectable groups or labels, such as radiolabels (e.g., $^{125}I$, $^{32}P$, $^{35}S$) or a chemiluminescent or fluorescent group. Similarly, the detectable group can be a substrate, cofactor, inhibitor or affinity ligand.

Binding of a test agent to LXR can also be tested indirectly with a cell-based assay. For example, a DNA-binding domain of the nonreceptor transcription factor GAL4 can be fused to the ligand-binding domain of LXR (e.g., LXRalpha). The resultant construct is introduced into a host cell (e.g., the 293 cells) together with a reporter construct (e.g., a UAS-containing luciferase reporter construct). The transfected cells are then treated with libraries of test agents, and reporter polypeptide activity (e.g., luciferase activity) is measured. Effects of individual test agents on the reporter polypeptide activity are evaluated relative to a control (i.e., when no test compound is present).

The cell-free ligand sensing assay (LiSA) can also be employed to identify novel LXR agonists. It can be performed as described in the art, e.g., Collins et al., J Med. Chem. 45: 1963-6, 2002; and Spencer et al., J. Med. Chem. 44: 886-97, 2001. This assay measures the ligand-dependent recruitment of a peptide from the steroid receptor coactivator 1 (SRC1) to the nuclear receptor. With this assay (LiSA), the structural requirements for activation of the LXR receptor by test agents can be studied.

Other than or in addition to detecting a direct binding of a test agent to an LXR polypeptide, potential LXR agonists for use in the methods of the present invention can also be examined for ability to activate other bioactivities or cellular activities of the LXR receptor. Test agents which activate LXR receptor can be identified by monitoring their effects on a number of LXR cellular activities. LXR cellular activities include any activity mediated by activated LXR receptor (e.g., transcriptional regulation of a target gene). For example, LXR trans-activate expression of a number of target genes (e.g., ABCA1), inhibit fibroblast differentiation to adipocytes, modulate the production of muscle-specific enzymes, e.g., creatine kinase, modulate glucose uptake by cells, and stimulate myoblast cell proliferation. The degree to which a test agent activates an LXR receptor can be identified by testing for the ability of the agent to enhance such LXR activities.

Thus, a novel LXR agonist can be identified by identifying a test agent that enhances expression of an LXR target gene (e.g., ABCA 1, ABCG 1, SREBP 1, or the cholesterol 7-hydroxylase gene). Methods for identifying test agents that induce an LXR target gene expression (e.g., increasing ABCA1 mRNA levels) have been disclosed in the art, e.g., Menke et al., Endocrinology 143: 2548-58, 2002; Sparrow et al., J. Biol. Chem. 277: 10021-7, 2002; and Murthy et al., J Lipid Res. 43: 1054-64, 2002.

Other than monitoring LXR target gene expression, LXR agonists can also be identified by examining other cellular activities stimulated by the LXR pathway. For example, LXR agonists modulate the protein level and hence activity of a muscle-specific enzyme, creatine kinase. Therefore, LXR agonists can be screened by examining test agents for ability to modulate creatine kinase activity, e.g., as described in Somjen et al., J Steroid Biochem Mol Biol 62: 401-8, 1997. The assay can be performed in a cell line, e.g., the mouse skeletal myoblast cell line or a primary chick myoblast cell line. Effects of test compounds on creatine kinase activity in the cultured cells can be measured in the cell lysates using a commercially available kit (available by Sigma, St Louis, Mo.).

Modulation of other cellular bioactivities of the LXR receptor can also be detected using methods well known and routinely practiced in the art. For example, the test agent can be assayed for their activities in increasing cholesterol efflux from cells such as macrophages (Menke et al., Endocrinology 143: 2548-58, 2002; and Sparrow et al., J. Biol. Chem. 277: 10021-7, 2002). Other assays include ligand-dependent transcription assays (Schmidt et al., Mol Cell Endocrinol 155: 51-60, 1999), methods for measuring the ability of LXR agonists to interfere with the differentiation process of pre-adipocytes (fibroblasts) to adipocytes (Plaas et al., Biosci Rep 1: 207-16, 1981; Hiragun et al., J Cell Physiol 134: 124-30, 1988; and Liao et al., 3 Biol Chem 270: 12123-32, 1995), or the ability to stimulate myoblast cell proliferation (Konishi et al., Biochemistry 28: 8872-7, 1989; and Austin et al., J Neurol Sci 101: 193-7, 1991). As a control, all these assays can include measurements before and after the test agent is added to the assay system.

Therapeutic Applications

The present invention provides methods for treatment of beta cell degeneration in a subject comprising administering a LXR agonist to said subject.

The methods also find application in treating a disease characterized by insufficient beta cells and thus insulin dysfunction (e.g., resistance, inactivity or deficiency) and/or insufficient glucose transport into cells. Such diseases include, but are not limited to diabetes, hyperglycemia and obesity. Treatment of beta cell degeneration is also useful for preventing or modulating the development of such diseases or disorders in a subject suspected of being, or known to be, prone to such diseases or disorders.

More particularly, as it now has been unexpectedly found that it can be possible to avoid the beta cells degeneration, the invention is also directed to a method for preventing type I diabetes in a subject, the method comprising administering to the subject an effective amount of a LXR agonist.

The LXR agonists to be used in these applications can be any of the known LXR agonists that have been described in the art. Alternatively, the therapeutic methods comprise screening test agents to identify novel LXR agonists as described above, and administering such novel agonists to treat beta cells degeneration or to treat the above noted diseases in a subject.

The present inventors observed that stopping beta cells degeneration can be achieved after application of an LXR agonist for a very short period of time, e.g., 21 days. However, when the objective is to enhance insulin sensitivity or to ameliorate symptoms of diabetes in a subject, a longer period of treatment is necessary. For such applications, the LXR agonist is typically administered to a subject for a continued period of time, e.g., at least 30 days, 60 days, 90 days, or longer.

The invention concerns also a new method with an improved compliance. It is well known that the diabetic subject have to take a high number of drugs. The present invention permits to reduce the number of drugs to be taken, and even permits to stop the treatment once the glycemia and/or HbA1c value is stabilised or insulin sensitivity is recovered.

Thus the present invention is also directed to a method for treating or ameliorating diabetes, the method comprising measuring circulating glucose level and/or HbA1c in the subject and administering daily to the subject an effective amount of a LXR agonist until stabilisation of the glycemia and/or HbA1c, then stopping the treatment once the glycemia and/or HbA1c is stabilised.

The LXR agonist is preferably administered to the subject daily for at least 30 days. It can also be administered for at least 60 days, 90 days, or longer.

The daily treatment can optionally be reconducted if the glycemia and/or HbA1c is no more stabilised or insulin sensitivity is lost.

Methods for measuring circulating glucose level are the methods well known in the prior art and any kind of methods can be used.

Pharmaceutical Compositions (or Medicament)

The LXR agonists of the present invention can be directly administered under sterile conditions to the subject to be treated. The modulators can be administered alone or as the active ingredient of a pharmaceutical composition. Therapeutic composition of the present invention can be combined with or used in association with other therapeutic agents. For example, a subject may be treated with an LXR agonist along with other conventional anti-diabetes drugs. Examples of such known anti-diabetes drugs include Actos (pioglitizone, Takeda, Eli Lilly), Avandia (rosiglitazone, Smithkline Beacham), Amaryl (glimepiride, Aventis), Glipizide Sulfonlyurea (Generic) or Glucotrol (Pfizer), Glucophage (metformin, Bristol Meyers Squibb), Glucovance (glyburide/metformin, Bristol Meyers Squibb), Glucotrol XL (glipizide extended release, Pfizer), Glyburide (Micronase; Upjohn, Glynase; Upjohn, Diabeta; Aventis), Glyset (miglitol, Pharmacia & Upjohn), Metaglip (glipizide+metformin; fixed combination tablet), Prandin (repaglinide, NOVO), Precose (acarbose, Bayer), Rezulin (troglitazone, Parke Davis), and Starlix (nateglinide, Novartis).

A subject may also be treated with an LXR agonist along with GLP-1 analogues and derivatives. Such GLP-1 analogues and derivatives which can be used according to the present invention includes those referred to in WO 99/43705 (Novo Nordisk A/S), WO 99/43706 (Novo Nordisk A/S), WO 99/43707 (Novo Nordisk A/S), WO 98/08871 (Novo Nordisk A/S), WO 99/43708 (Novo Nordisk A/S), WO 99/43341 (Novo Nordisk A/S), WO 87/06941 (The General Hospital Corporation), WO 90/11296 (The General Hospital Corporation), WO 91/11457 (Buckley et al.), WO 98/43658 (Eli Lilly & Co.).

Pharmaceutical compositions of the present invention typically comprise at least one active ingredient together with one or more acceptable carriers thereof. Pharmaceutically carriers enhance or stabilize the composition, or to facilitate preparation of the composition. Pharmaceutically acceptable carriers are determined in part by the particular composition being administered (e.g., nucleic acid, protein, or modulatory compounds), as well as by the particular method used to administer the composition. They should also be both pharmaceutically and physiologically acceptable in the sense of being compatible with the other ingredients and not injurious to the subject. This carrier may take a wide variety of forms depending on the form of preparation desired for administration, e.g., oral, sublingual, rectal, nasal, or parenteral.

There are a wide variety of suitable pharmaceutically acceptable carriers to practice the present invention (see, e.g., Remington: The Science and Practice of Pharmacy, Mack Publishing Co., 20th ed., 2000). Without limitation, they include syrup, water, isotonic saline solution, 5% dextrose in water or buffered sodium or ammonium acetate solution, oils, glycerin, alcohols, flavoring agents, preservatives, coloring agents starches, sugars, diluents, granulating agents, lubricants, and binders, among others. The LXR agonist can also be complexed with carrier proteins such as ovalbumin or serum albumin prior to their administration in order to enhance stability.

The pharmaceutical compositions can be prepared in various forms, such as granules, tablets, pills, suppositories, capsules, suspensions, salves, lotions and the like. The concentration of therapeutically active compound in the formulation may vary from about 0.1-100% by weight. Therapeutic formulations are prepared by any methods well known in the art of pharmacy. See, e.g., Gilman et al., eds., Goodman and Gilman's: The Pharmacological Bases of Therapeutics, $8^{th}$ ed., Pergamon Press, 1990; Remington: The Science and Practice of Pharmacy, Mack Publishing Co., $20^{th}$ ed., 2000; Avis et al., eds., Pharmaceutical Dosage Forms: Parenteral Medications, published by Marcel Dekker, Inc., N.Y., 1993; and Lieberman et al., eds., Pharmaceutical Dosage Forms: Disperse Systems, published by Marcel Dekker, Inc., N.Y., 1990.

A pharmaceutical composition of the invention is formulated to be compatible with its intended route of administration. Examples of suitable routes of administration include parenteral, e.g., intravenous, intradermal, subcutaneous, oral (e.g., inhalation), transdermal (topical), transmucosal, and rectal administration. For parenteral administration, the LXR agonists of the present invention may be formulated in a variety of ways. Aqueous solutions of the modulators may be encapsulated in polymeric beads, nanoparticles or other injectable depot formulations known to those of skill in the art. Additionally, the compounds of the present invention may also be administered encapsulated in liposomes. The compositions, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such a diacetylphosphate, stearylamine, or phosphatidic acid, and/or other materials of a hydrophobic nature.

The compositions may be supplemented by other active pharmaceutical ingredients, where desired. Optional antibacterial, antiseptic, and antioxidant agents may also be present in the compositions where they will perform their ordinary functions. In some applications, the LXR agonists are prepared with carriers that will protect the compound against rapid elimination from the body, such as a controlled release formulation, including implants and microencapsulated delivery systems. A sustained release material such as glyceryl monostearate or glyceryl distearate, alone or with a wax can be included in the compositions. Biodegradable, biocompatible polymers can also be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

The pharmaceutical compositions can be included in a container, pack, or dispenser together with instructions for administration.

Dosages

Subjects suffering from diabetes or related disorders are typically treated with pharmaceutical compositions of the present invention for a continued period of time (e.g., at least 30 days, 60 days, 90 days, or longer). The pharmaceutical compositions comprise a pharmaceutically effective amount or prophylactically effective amount of a LXR agonist. The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human.

A suitable therapeutic dose can be determined by any of the well-known methods such as clinical studies on mammalian species to determine maximum tolerable dose and on normal human subjects to determine safe dosage. Particularly, the dosage amount of a LXR ligand that a subject receives can be selected so as to achieve the beta cell regeneration; the dosage a subject receives may also be titrated over time in order to stabilise glycaemia and/or HbA1c or to recover insulin sensitivity. Toxicity and therapeutic efficacy of LXR agonists can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. LXR agonists that exhibit large therapeutic indices are preferred. While LXR agonists that exhibit toxic side effects may be used, care should be taken to design a delivery system that targets such LXR agonists to the site of affected tissue in order to minimize potential damage to uninfected cells and, thereby, reduce side effects.

The data obtained from the cell culture assays and animal studies can be used in formulating a range of dosages for use in humans. The dosage of such compounds lies preferably within a range of circulating concentrations that include the $ED_{50}$ with little or no toxicity. The dosage may vary within this range depending upon the dosage form employed and the route of administration utilized. For any LXR agonist used in the method of the invention, the therapeutically effective dose can be estimated initially from cell culture assays. A dose may be formulated in animal models to achieve a circulating plasma concentration range that includes the $IC_{50}$ (i.e., the concentration of the test LXR agonists which achieves a half-maximal inhibition of symptoms) as determined in cell culture. Such information can be used to more accurately determine useful doses in humans. Levels in plasma may be measured, for example, by high performance liquid chromatography.

In general, except under certain circumstances when higher dosages may be required, the preferred dosage of a LXR agonist usually lies within the range of from about 0.001 to about 1000 mg, more usually from about 0.01 to about 500 mg per day. The preferred dosage and mode of administration of a LXR agonist can vary for different subjects, depending upon factors that can be individually reviewed by the treating physician, such as the condition or conditions to be treated, the choice of composition to be administered, including the particular LXR agonist, the age, weight, and response of the individual subject, the severity of the subject's symptoms, and the chosen route of administration. As a general rule, the quantity of a LXR agonist administered is the smallest dosage that effectively and reliably prevents or minimizes the conditions of the subjects. Therefore, the above dosage ranges are intended to provide general guidance and support for the teachings herein, but are not intended to limit the scope of the invention.

In some applications, a first LXR agonist is used in combination with a second LXR agonist or a known anti-diabetes drug in order to achieve therapeutic effects that cannot be achieved when just one LXR agonist is used individually.

Ex Vivo Treatment

The invention further features a method of inhibiting the loss of a beta cell in pancreatic islet tissue by contacting pancreatic islet tissue with a LXR agonist. By decreasing the loss is meant that the pancreatic tissue has 10%, 20%, 30%, 40% or more beta cells in the presence of the LXR agonist compared to the absence of the LXR agonist.

The invention also features a method of increasing the viability or proliferation of pancreatic islet cells by contacting a cell with a LXR agonist. Additionally, viability of pancreatic islet cells is increased by administering to a transplant recipient a LXR agonist. The pancreatic islet cells are primary islet cells. Alternatively, the cells are transplanted donor pancreatic cells. By viability is meant that the cell is excludes a vital dye, such as trypan. Viable cells are also capable of proliferation, differentiation, growth and development. Viability is measured by methods known in the art such as trypan blue staining. The cells are contacted in vivo, in vitro or ex vivo. The LXR agonist is administered locally to a transplanted site. Alternatively the LXR agonist is administered systemically. The LXR agonist is administered to the transplant recipient prior to or after transplantation of donor pancreatic islet cells. Optionally, the LXR agonist is administered to the transplant recipient concurrently with the transplantation of donor pancreatic.

Also included in the invention are methods of inhibiting cell death by contacting the cell with a LXR agonist. The cells are contacted in vivo, in vitro or ex vivo. The cell is a pancreatic cell such as a pancreatic islet beta cell. The cell death is oxidative stress induced cell death or apoptotic cell death.

EXAMPLES

Figure 1:
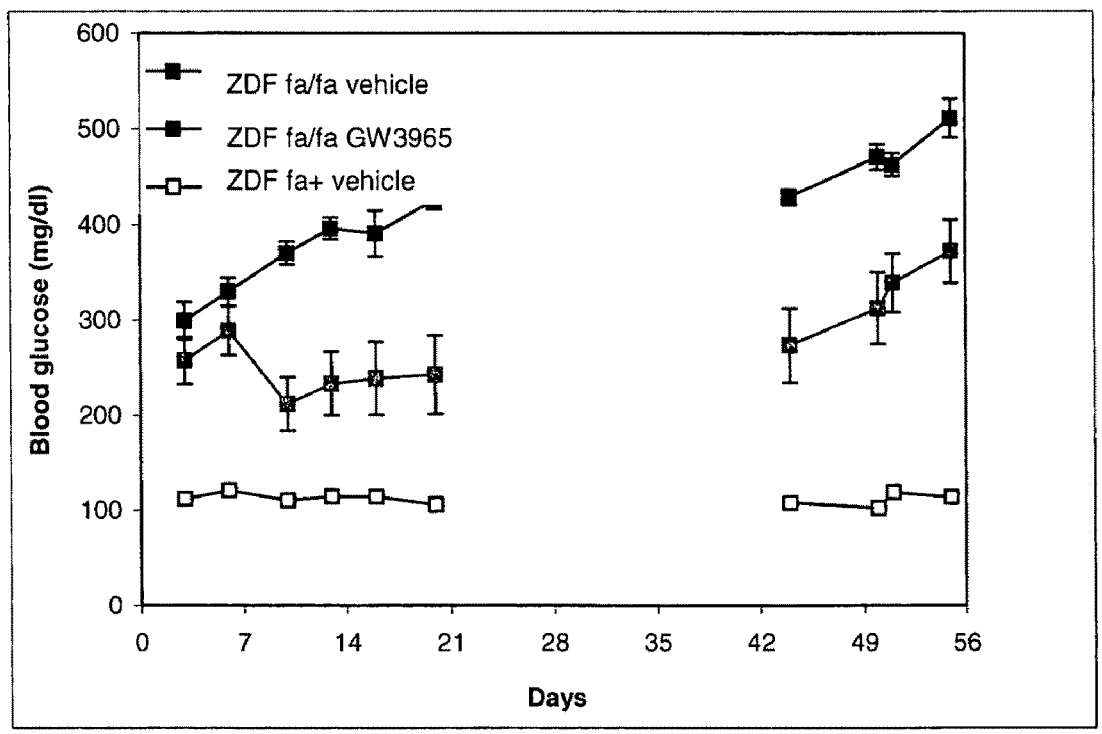
FIG. 1 shows the effect of GW3965 (10 mg/kg) orally administered in ZDF rats for 3 weeks on plasma glucose and after the end of treatment.

The following examples are offered to illustrate, but not to limit the present invention.

Animals

The male Zucker Diabetic Fatty fa/fa (ZDF) rat is a model of Type II diabetes. The rats are insulin resistant but normoglycemic from birth and they develop diabetes from about week 7 to week 10 of age. During the transitional period, the animals go through a state of impaired glucose tolerance. Although the animals are hyperinsulinemic before diabetes onset and during the early stages of diabetes, they later lose glucose-stimulated insulin secretion and finally become almost completely insulinopenic.

Male ZDF fa/fa and ZDF fa+ rats were obtained from Genetic Models (Indianapolis, Ind.), at the age of 6 weeks and used in the experiments at 12 weeks of age, after 3 weeks of oral treatment with vehicle or GW3965 (10 mg/kg). Compounds were given once daily (at 17 h) via oral gavage. At the time of their use, the ZDF fa/fa rats weighed 310-350 g, whereas the age-matched ZDF fa+ rats weighed 245-285 g. ZDF fa+ and ZDF fa/fa animals had free access to diabetogenic chow (Purina 5008). Animals were housed 5 per cage in a temperature and humidity-controlled room with a 12/12-h light-dark cycle. Blood samples were taken 16 h after compound administration via the tail vein and measured on a Konelab 300 (Labsystem) clinical chemistry analyzer.

NOD (non-obese diabetes) mice is an experimental model of spontaneous resembling human Type I (insulin-dependent) diabetes, which results from the progressive islet invasion and beta cells destruction by autoreactive T cells. This spontaneous diabetes model offers a unique opportunity of studying the autoreactive T cells involved in the process of beta cell destruction and of settling preventive strategies before clinical onset of the disease.

Preparation of Rat Pancreatic Islets

Rat pancreatic islets were prepared by collagenase digestion and density gradient purification. The enzyme collagenase type XI (Sigma Chemical, St. Louis, Mo.) was used for digestion of the pancreas. After an overnight fast, animals were deeply anesthetized and killed. Then, the pancreatic duct was cannulated, and 20 ml of the digestion solution at 37° C. (collagenase 30 mg/ml dissolved in 20 ml Hanks' balanced salt solution [HBSS]) (Sigma Chemical, St. Louis, Mo.) was slowly injected to distend the tissue. After distension, the pancreas was placed into a 20-ml glass beaker containing 5 ml of the digestion solution at 37° C. that was set into a shaking water bath at 37° C. for 8 minutes. After centrifugation at 633 g for 1 min at 4° C., the supernatant was removed and the islets were washed three times with HBSS by centrifugation at 633 g for 1 min at 4° C. For the purification procedure, the islets were resuspended in 4 ml of 80% Histopaque 1.077 (Sigma) and 4 ml HBSS. After centrifugation at 1943 g for 20 min at 4° C., the islets were recovered at the interface between the Histopaque and the HBSS layers. The islets were resuspended in RPMI 1640 medium containing 11 mM glucose, 10% of FCS, penicillin (100 U/ml), streptomycin (100 μg/ml) and L-glutamine (2 mM) and overnight cultured at 37° C. in a $CO_2$ incubator.

Evaluation of Apoptosis by Measurement of DNA Fragments

The apoptosis of islet cells was assessed by the Cell Death Detection enzyme-linked immunosorbent assay (ELISA) plus Kit from Roche, according to the procedures recommended by the manufacturer and applied to rat islet experiment. After an overnight incubation in RPMI 1640 medium containing 11 mM glucose, 10% of FCS, penicillin (100 U/ml), streptomycin (100 μg/ml) and L-glutamine (2 mM), groups of 10 islets were incubated for 30 min with a lysis buffer at room temperature and then centrifuged at 200 g for 10 min at 4° C. for the apoptosis. Aliquots of the supernatant (20 μl) were placed into microtiter plate wells coated with streptavidin. A total of 80 μl of a mixture containing anti-histone-biotin antibody and anti-DNA-peroxidase antibody was then added, and incubation was allowed for 120 min at 37° C. Then, the preparations were washed and 100 μl of a solution containing ABTS (2,2'-azino-di[3-ethylbenzthiazalin-sulfonate]) (the substrate for peroxidase) was added. At the end of the 5-min incubation, absorbance of samples was read spectrophotometrically at 405 nm. The results were expressed as a percent of internal standard (nucleosomal particles).

Evaluation of Apoptosis by TUNEL Staining

Islet cell apoptosis was determined by transferase-mediated dUTP nick-end labeling (TUNEL) staining. Cell death was identified by 3' in situ end labeling of fragmented DNA with biotinylated deoxyuridine-triphosphate. Each pancreatic piece was cut throughout its length into 5 μm thick sections, which were collected on gelatin-coated slides. Four sections at regular intervals were picked in both head and tail pieces. After digestion with Proteinase K (2 μg/ml; Sigma), sections were consecutively washed in TdT buffer (0.5 mol/l cacodylate [pH 6.8], 1 mmol/l cobalt chloride, 0.15 mol/l NaCl) and then incubated at 37° C. with TdT (25U; Boehringer-Mannheim, Mannheim, Germany) and biotinylated dUTP (1 nmol/μl). After washing in TB buffer (300 mmol/l NaCl, 30 mmol/l sodium citrate) to terminate the reaction, incorporation of biotinylated dUTP was detected by a modification of the avidin-biotin complex method. Horseradish peroxidise-conjugated streptavidin-biotin complex was applied (Vector Laboratories). The sections were then developed using DAB as chromogen and lightly counterstained with hematoxylin and mounted in dePex (BDH Laboratory, Poole, England).

Glucose-Stimulated Insulin Secretion and Islet Insulin Content

After a 30-min preincubation period at 37° C. for 30 min in Krebs-Ringer bicarbonate (KRB)-HEPES solution (129 mM NaCl, 4.8 mM KCl, 1.2 mM $MgSO_4$, 1.2 mM $KH_2PO_4$, 2.5 mM $CaCl_2$, 5 mM $NaHCO_3$, and 10 mM HEPES at pH 7.4) containing 0.5% BSA and without glucose. Batches of 3 islets of comparable size were placed into microtiter plate wells containing 200 μl of KRB-HEPES solution containing 0.5% BSA and 3.3 mM glucose at 37° C. for 1 hour under agitation and atmosphere of 5% $CO_2$ and 95% $O_2$. At the end of this challenge, the medium was completely removed and replaced with KRB-HEPES containing 16.7 mmol/l glucose. After an additional 1-hour incubation, the medium was removed and frozen. Insulin content was measured in the same islets after an overnight alcohol-acid extraction (Ethanol 75%+HCl 0.15 N). Insulin concentrations in the different media were determined by rat insulin ELISA test (Insulin Rat Elite plus, MERCODIA).

Real-Time Quantitative Reverse Transcription-PCR

Pancreatic and duodenal homeobox gene 1, Pdx1 (Genbank: NM_022852) and facilitated glucose transporter, member 2, Glut2 (Genbank: NM_012879) gene expression were measured by real time quantitative RT-PCR.

Total RNAs from fresh isolated rat pancreatic islets were prepared using Rneasy 96 Kit according to the manufacturer's protocol (Qiagen, France), treated with Dnase I to remove contaminating DNA (Stratagene, France), and quantified using the iScript cDNA Synthesis and iQ SYBR Green Supermix kits (Biorad, france). Real-time quantitative RT-PCR was performed using the iCycler Detection System instrument and software (Bio-Rad). As the predicted size of the amplified cDNAs and the Tm values for the primers were similar, uniform amplification conditions were applied (ie. annealing at 60° C.). Specificity of amplified products was monitored by performing melting curves at the end of each amplification. Expression levels were quantified (total RNA units) by generating a six-point serial standard curve. RNA samples were normalized for comparison by determining 18S rRNA levels.

```
Primer sequences
PDX1 (forward):      CCACAGCCCTCCAGCATCG
                     (SEQ ID NO: 1)

PDX1 (reverse):      CAGACCCGCTCACCCTCAG
                     (SEQ ID NO: 2)

Glut2 (forward):     ACCAGCACATACGACACCAGAC
                     (SEQ ID NO: 3)

Glut2 (reverse):     GACACAGACAGAGACCAGAGCATAG
                     (SEQ ID NO: 4)

18S (forward):       CGTCTGCCCTATCAACTTTCG
                     (SEQ ID NO: 5)

18S (reverse):       GATGTGGTAGCCGTTTCTCAG
                     (SEQ ID NO: 6)
```

Data Analysis

The data are expressed as mean±SEM. The comparisons between various groups were obtained by the Student t-test. Differences in $p<0.05$ between experimental groups were considered statistically significant. For comparisons, ZDF fa/fa group is compared with ZDF fa+ group and ZDF fa/fa GW3965 group is compared with ZDF fa/fa group.

Pancreatic Sections and Histologic Analysis

Non fasted mice were killed two days after the last administration of compounds. Pancreatic glands were excised and processed for conventional histological studies after fixation in Bouin's alcoholic solution. Five μm sections were stained with haematoxylin-eosin as described previously by Thivolet C. H. et al., 1991, Diabetologia, 34, 314-319.

Example 1

Effect of GW3965 (10 mg/kg) Orally Administered in ZDF Rats for 3 Weeks on Plasma Glucose and After the End of Treatment Patterns of changes in plasma glucose are shown in FIG. 1. At the beginning of the study, glycemia was similar in vehicle- and GW3965-treated ZDF rats.

At day 6, plasma glucose levels in the vehicle-treated group increased above 400 mg/ml. GW3965 treatment significantly prevented this rise and maintained glycemia at low level up to the end of treatment at day 21.

From day 21 to the end of the experiment, the animals did not receive any treatment. At day 44, glycemia was still significantly reduced in ZDF rats that were previously treated with GW3965. This indicates that the long-lasting control of glycemia which follows a limited period of treatment with GW3965, likely resulted from a restoration of beta cell function and mass in agreement with ex vivo data. This example supports the proposal of new mode of treatment based on administration of a LXR agonist for limited periods of time to diabetic patients.

Results show that while the effect on triglycerides is reduced after stopping the treatment, the decrease of blood glucose was maintained for more than a month. LXR agonist ligands can thus be administered either as a loading dose for one or several days and subsequent reloading administration on a weekly basis or longer depending the loading dose, or alternatively every other day or alternatively every other weeks (or several days).

Example 2

Glucose-Stimulated Insulin Secretion in Pancreatic Islets Isolated from ZDF Rats Orally Treated for 3 Weeks with GW3965 (10 mg/kg)

Figure 2:
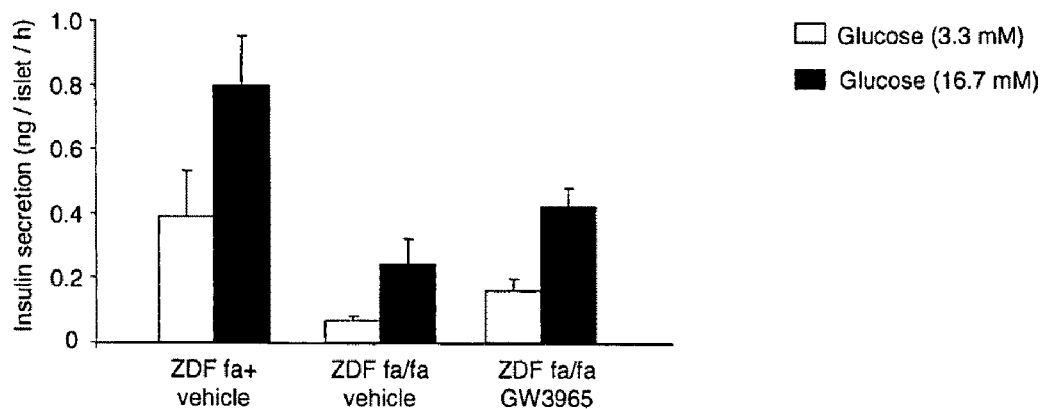
FIG. 2 shows the effect of GW3965 (10 mg/kg) orally administered in ZDF rats for 3 weeks on glucose-stimulated insulin secretion in isolated pancreatic islets.

The results are presented in FIG. 2. In the presence of 3.3 mmol/l and 16.7 mmol/l glucose, insulin secretion of ZDF compared to fa+ rat islets was reduced by 82.6 and 69.6%, respectively. In GW3965-compared to vehicle-treated ZDF rat islets, insulin secretion in response to 3.3 mmol/l and 16.7 mmol/l glucose significantly increased by 133.8% and 74.5%, respectively. Thus, it is shown that glucose-stimulated insulin secretion of ZDF rat pancreatic islets is improved by a LXR agonist.

Example 3

Figure 3:
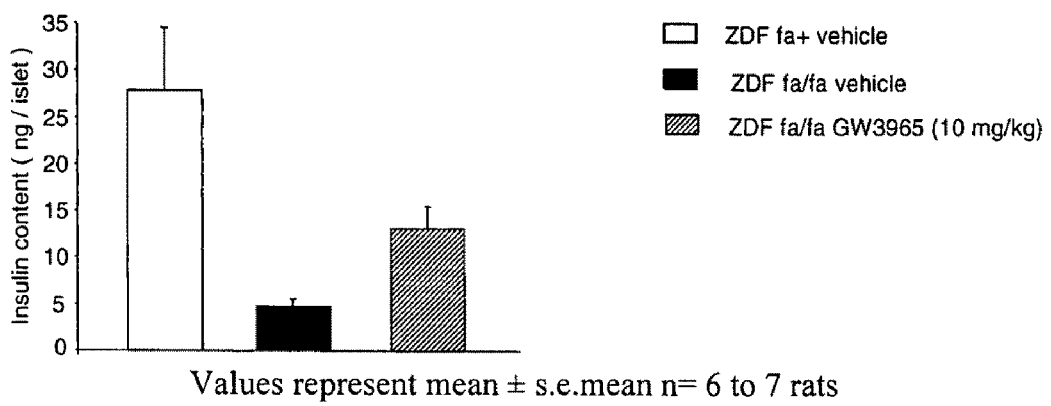
FIG. 3 shows the effect of GW3965 (10 mg/kg) orally administered in ZDF rats for 3 weeks on insulin content of isolated pancreatic islets.

Effect of GW3965 (10 mg/kg) Orally Administered to ZDF Rats for 3 Weeks on Insulin Content of Isolated Pancreatic Islets The results are presented in FIG. 3. Insulin content was strongly reduced in the islets of ZDF rats compared to the islets of fa+ rats (4.78±0.86 vs 27.74±6.85 ng/islet). Insulin content of the islets of ZDF treated with GW3965 (10 mg/kg) was significantly increased in comparison with the islets of ZDF treated with the vehicle (13.05±2.49 vs 4.78±0.86 ng/islet).
This example demonstrates that the insulin content of pancreatic islets is increased with a LXR agonist.

Example 4

Figure 4:
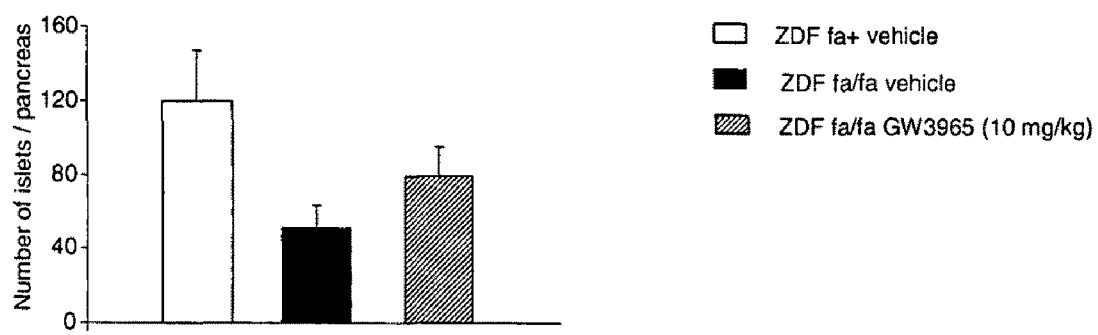
FIG. 4 shows the effect of GW3965 (10 mg/kg) orally administered in ZDF rats for 3 weeks on number of harvested pancreatic islets.

Effect of GW3965 (10 mg/kg) Orally Administered to ZDF Rats for 3 Weeks on Number of Harvested Pancreatic Islets The results are presented in FIG. 4. The number of pancreatic islets harvested in ZDF rats was lower than that collected in fa+ rats (51±13 and 120±28 islets/rat, respectively). GW3965-treated ZDF rats had an increased number of pancreatic islets compared to vehicle-treated ones (80±16 and 51±13 islets/rat, respectively).

Thus, the number of pancreatic islets is increased following an in vivo treatment with a LXR agonist.

Example 5

Effect of GW3965 (10 mg/kg) Orally Administered to ZDF Rats for 4 Weeks on Apoptosis in Isolated Pancreatic Islets and Pancreatic Sections In this example, the apoptosis rate of pancreatic islets was investigated. The results are presented in FIG. 5 (see panel A). DNA fragments, as measured by a specific ELISA assay after an overnight culture in RPMI medium, were significantly increased in islets of ZDF rats in comparison with the islets of control fa+ rats (43.1±9.2% versus 19.9±6.2%). Apoptosis in pancreatic islets isolated from GW39065-compared to vehicle-treated ZDF rats was reduced (34.0±7.5% and 43.1±9.2%, respectively).

Figure 5:
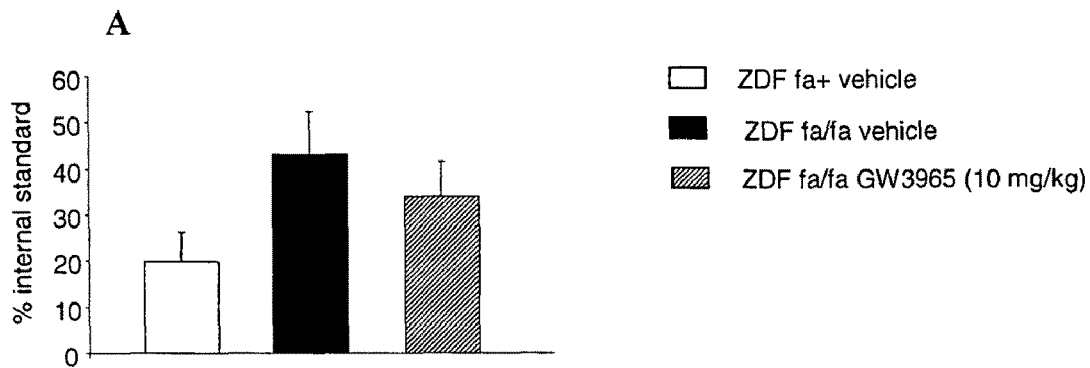
FIG. 5 shows the effect of GW3965 (10 mg/kg) orally administered in ZDF rats for 4 weeks on apoptosis in isolated pancreatic islets and pancreatic sections.
Figure 5:
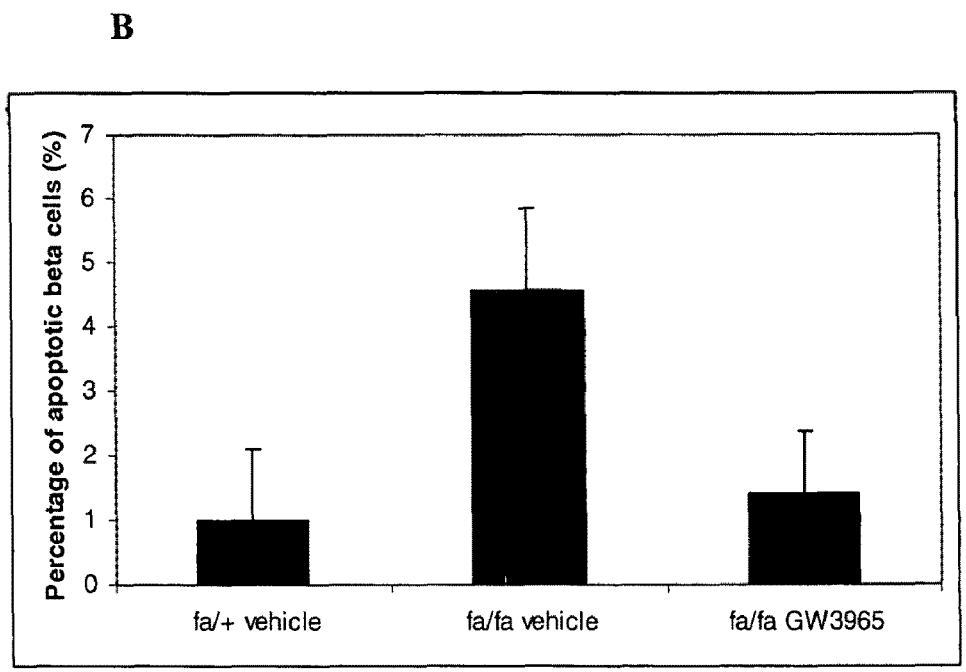

Apoptosis have also been estimated using the TUNEL staining method on pancreatic sections of 5 animals of 8 weeks-old ZDF rats treated with GW3965 at 10 mg/kg for 4 weeks. Results are represented in FIG. 5 (see Panel B) and show that apoptosis in pancreatic sections from GW39065-treated ZDF rats was significantly reduced compared with that of vehicle-treated control mice (1.41±0.96% and 4.55±1.29% of apoptosis, respectively ($p<0.05$).

An oral in vivo treatment with an LXR agonist permits to reduce the apoptosis of corresponding isolated pancreatic islets. Specifically, since beta cells represents 85-95% of the pancreatic islet, these results show that LXR agonist administration significantly reduce beta cells apoptosis.

Example 6

Figure 6:
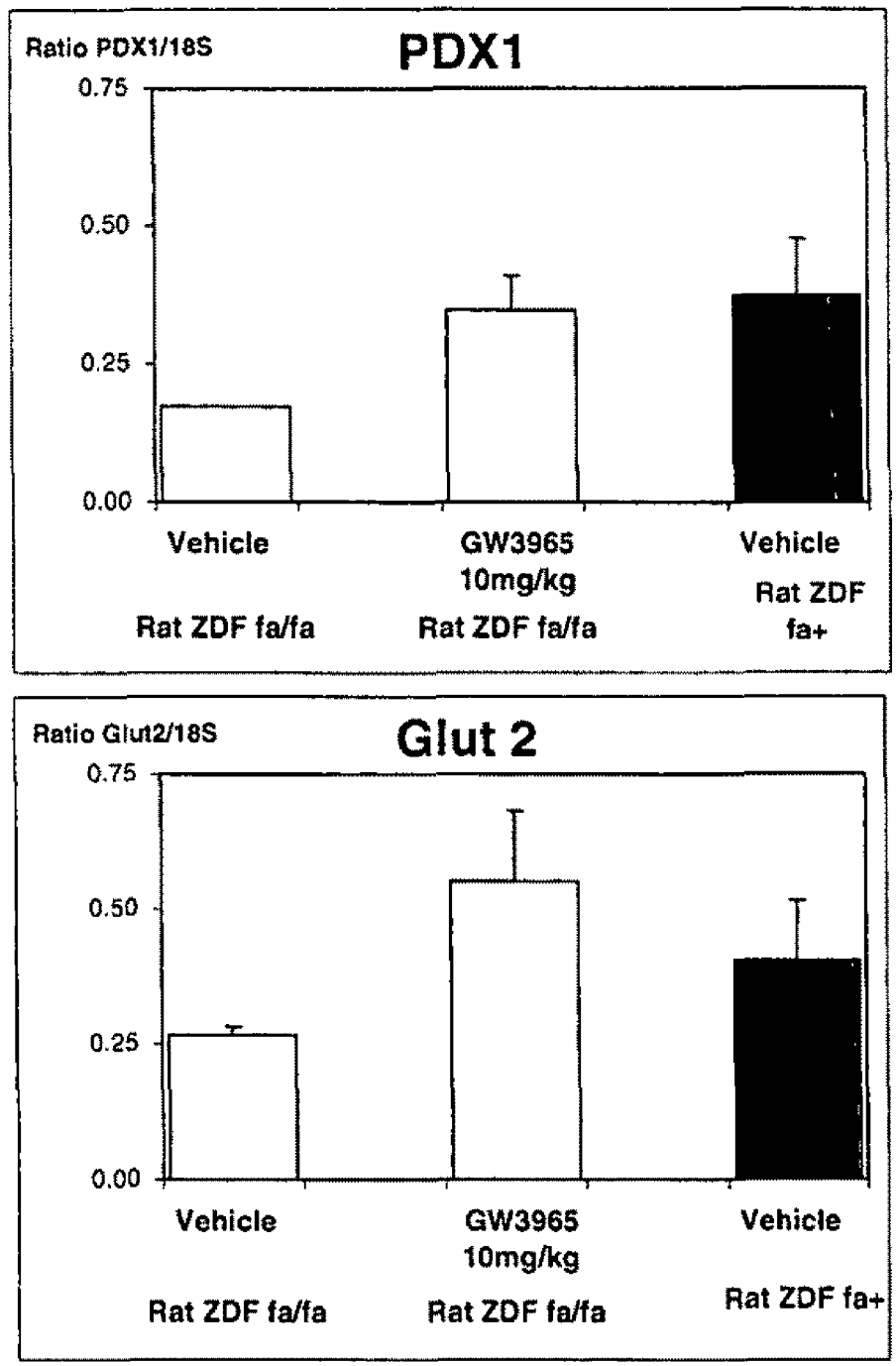
FIG. 6 shows the effect of GW3965 on PDX1 and GLUT2 mRNA expression.

Effect of GW3965 on PDX1 and GLUT2 mRNA Expression (FIG. 6)

In this example, the mRNA expression of PDX1 and Glut2 was determined. As previously described, PDX1 and Glut2 are markers of the regeneration of beta cells. PDX1 and Glut2 mRNA expression was markedly reduced in the islets of ZDF vs control fa+ rats (0.17 vs 0.38±0.21 and 0.27 vs 0.40±0.22, respectively). PDX1 and Glut2 mRNA expression was increased in islets isolated from GW3965-compared to vehicle-treated ZDF rats. Values were 0.35±0.11 for PDX1 and 0.55±0.23 for Glut2.

This example demonstrates that beta-cells of pancreatic islets are undergoing regeneration upon treatment with a LXR agonist.

Example 7

Figure 7:
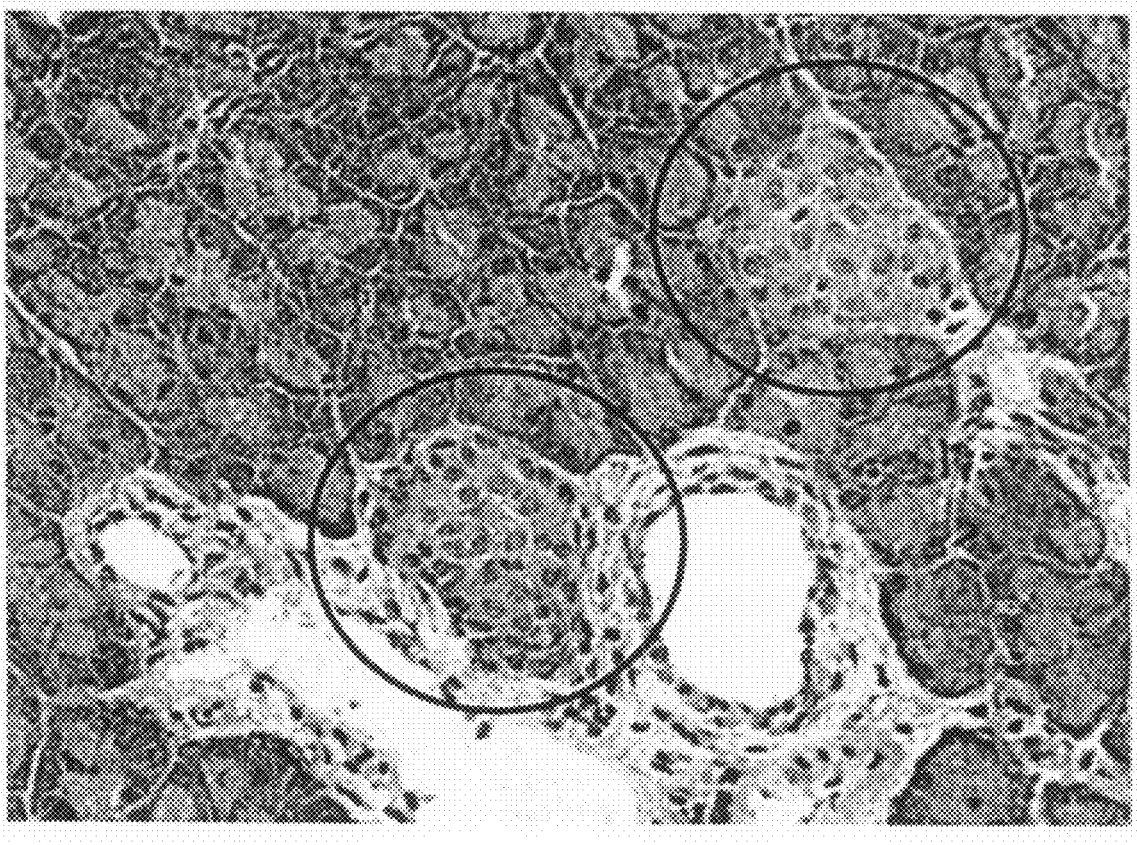
FIG. 7 shows the effect of GW3965 (50 mg/kg) on the regeneration of beta cells in NOD mice.

Effect of GW3965 (50 mg/kg) on the Regeneration of Beta Cells in NOD Mice (FIG. 7)

NOD mice of 4 weeks old have been treated for 4 weeks (5 days/7) with vehicle or GW3965 at 50 mg/kg. Pancreatic histological studies have been carried out as described above.

As clearly shown by the formation of new islets identified into circles in FIG. 7, beta-cells of pancreatic islets are undergoing regeneration upon treatment with a LXR agonist. In addition, the regeneration of beta cells occurs with a pancreatic islet morphological structure equivalent to that of normal pancreatic islets.

Example 8

Figure 8:
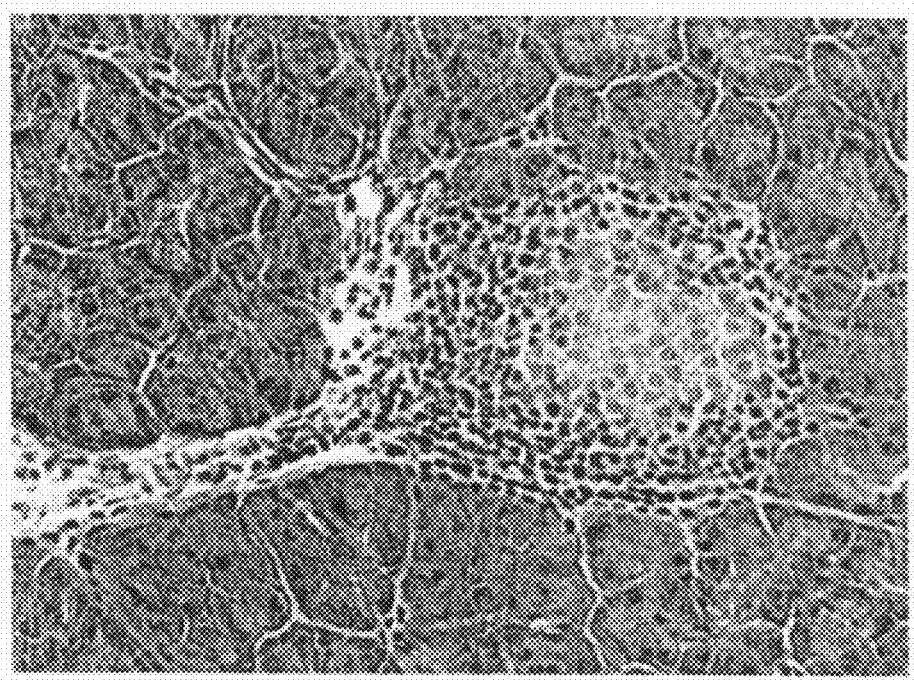
FIG. 8 shows the effect of GW3965 (50 mg/kg) on the insulitis development in NOD mice and wherein panel A represents pancreatic sections of control NOD mice treated with the vehicle only and panel B illustrates pancreatic sections of GW3965-treated NOD mice.
Figure 8:
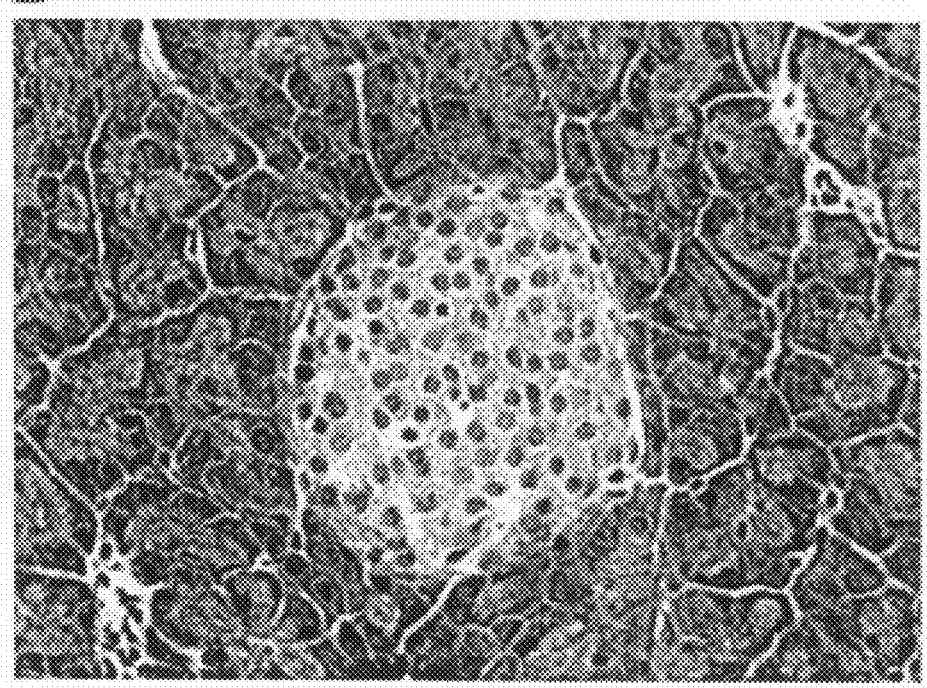

Effect of GW3965 (50 mg/kg) on the Insulitis Development in NOD Mice (FIG. 8)

The evolution of insulitis was analysed in pancreas. Five states of insulitis were commonly described: state 0 characterized by normal islets without monocytes infiltration (T lymphocytes), state 1 corresponding to a periinsulitis, state 2 with insulitis inferior to 50%, state 3 with insulitis superior to 50% and state 4 with apoptosis. State 4 was not observed in 8 weeks old mice, this state appeared at around 9-10 weeks.

NOD mice of 4 weeks old have been treated for 4 weeks (5 days/7) with vehicle or GW3965 at 50 mg/kg. Pancreatic histological studies have been carried out as described above.

As shown in panel A, pancreatic sections of control NOD mice treated with the vehicle only exhibit insulitis whereas the pancreas of GW3965-treated NOD mice appears protected against the lymphocytes infiltration as illustrated in panel B. Indeed, 94% of normal islets was observed in the pancreas of GW3965-treated NOD mice whereas control NOD mice showed only 32% of normal islets (data not shown).

This example demonstrates that in vivo administration of LXR agonist GW3965 is able to inhibit the insulitis developed in NOD mice.

These examples show that a LXR agonist, GW3965, increases glucose-stimulated insulin secretion, insulin content and the number of islets, reduces beta-cell apoptosis and promotes regeneration of beta-cells in the severely diabetic ZDF rat. This was associated with an improvement of the diabetic state and a significant decrease of glycemia and HbA1c after 21 days of treatment.

In assessing potential mechanisms underlying the antidiabetic actions of LXR agonists, we discovered that treatment with GW3965 resulted in a significant reduction of beta-cell apoptosis and a significant increase of insulin content. Moreover we found a restoration of the mRNA level of PDX1 and Glut2 to control values as obtained in fa+ rats.

Thirty days after the end of the GW3965 treatment, we demonstrated that the compound had a long term protective and preventive effect on the development type II diabetes since plasma glucose was still maintained at low level.

Experimental results similar to those illustrated above in the examples have been obtained by using other LXR agonists such as T0901317 (data not shown).

It is understood that the examples and embodiments described herein are for illustrative purposes only and that various modifications or changes in light thereof will be suggested to persons skilled in the art and are to be included within the spirit and purview of this application and scope of the appended claims. Although any methods and materials similar or equivalent to those described herein can be used in the practice or testing of the present invention, the preferred methods and materials are described.

The invention claimed is:

1. A method of treating or inhibiting type I diabetes, said method comprising administering to a subject in need thereof a therapeutically effective amount of an LXR agonist selected from the group consisting of GW3965 and T0901317.

2. A method as claimed in claim 1, wherein the administering of the LXR agonist produces regeneration of beta cells.

3. A method as claimed in claim 1, wherein the administering of the LXR agonist produces an increase in viability of beta cells.

4. A method as claimed in claim 1, wherein said subject is a transplant recipient of transplanted donor pancreatic islet cells, and the administering of the LXR agonist produces an increase in viability of the transplanted donor pancreatic islet cells in the subject.

5. A method as claimed in claim 1, wherein the LXR agonist is administered orally.

6. A method as claimed in claim 1, wherein the LXR agonist is administered daily for at least 30 days.

7. A method of treating type I diabetes in a subject suffering therefrom, said method comprising
measuring circulating glucose level, or HbA1c level, or both, in the subject;
administering daily to the subject a therapeutically effective amount of an LXR, agonist selected from the group consisting of GW3965 and T0901317 until the measured circulating glucose level is maintained at a glucose target value less than or equal to 1.4 g/l, or until the measured HbA1c level is maintained at an HbA1c target value less than or equal to 7%, or both, for one month with at least two dosages;
thereafter stopping the administration of the LXR agonist; and
optionally recommencing the administration of the LXR agonist if the measured glucose level or HbA1c level exceeds either or both of the respective target values.

8. A method as claimed in claim 7, wherein the circulating glucose target value is less than or equal to 1.2 g/l.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial
<220> FEATURE:
<223> OTHER INFORMATION: PDX-1 forward primer

<400> SEQUENCE: 1
ccacagccct ccagcatcg                                                  19

<210> SEQ ID NO 2
<211> LENGTH: 19
<212> TYPE: DNA
<213> ORGANISM: Artificial
<220> FEATURE:
<223> OTHER INFORMATION: PDX-1 reverse primer

<400> SEQUENCE: 2
cagacccgct caccctcag                                                  19

<210> SEQ ID NO 3
<211> LENGTH: 22
<212> TYPE: DNA
<213> ORGANISM: Artificial
<220> FEATURE:
<223> OTHER INFORMATION: Glut-2 forward primer

<400> SEQUENCE: 3
accagcacat acgacaccag ac                                              22

<210> SEQ ID NO 4
<211> LENGTH: 25
<212> TYPE: DNA
```

```
<213> ORGANISM: Artificial
<220> FEATURE:
<223> OTHER INFORMATION: Glut-2 reverse primer

<400> SEQUENCE: 4
gacacagaca gagaccagag catag                                           25

<210> SEQ ID NO 5
<211> LENGTH: 21
<212> TYPE: DNA
<213> ORGANISM: Artificial
<220> FEATURE:
<223> OTHER INFORMATION: 18S forward primer

<400> SEQUENCE: 5
cgtctgccct atcaactttc g                                               21

<210> SEQ ID NO 6
<211> LENGTH: 21
<212> TYPE: DNA
<213> ORGANISM: Artificial
<220> FEATURE:
<223> OTHER INFORMATION: 18S reverse primer

<400> SEQUENCE: 6
gatgtggtag ccgtttctca g                                               21
```